US006701918B2

(12) United States Patent
Fariss et al.

(10) Patent No.: US 6,701,918 B2
(45) Date of Patent: *Mar. 9, 2004

(54) MAGNETICALLY GUIDED DEVICE FOR INSERTION THROUGH A NASAL PASSAGEWAY

(75) Inventors: Bruce L. Fariss, Knoxville, TN (US); Ivan N. Cooper, Knoxville, TN (US); D. Matthew Sellers, Knoxville, TN (US)

(73) Assignee: Ibionics Corporation, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/229,231

(22) Filed: Aug. 27, 2002

(65) Prior Publication Data

US 2003/0154986 A1 Aug. 21, 2003

Related U.S. Application Data

(63) Continuation-in-part of application No. 10/207,602, filed on Jul. 29, 2002, which is a continuation-in-part of application No. 10/078,133, filed on Feb. 19, 2002.

(51) Int. Cl.$^7$ .............................................. A61M 16/00
(52) U.S. Cl. .............................. 128/200.26; 128/207.14
(58) Field of Search .................. 128/200.26, 207.14, 128/207.15, 207.29

(56) References Cited

U.S. PATENT DOCUMENTS

| | | | | | |
|---|---|---|---|---|---|
| 2,463,149 A | * | 3/1949 | Caine | ..................... | 128/200.26 |
| 2,541,402 A | * | 2/1951 | Caine | ..................... | 128/200.26 |
| 2,862,498 A | * | 12/1958 | Weekes | ................. | 128/207.14 |
| 3,314,431 A | * | 4/1967 | Smith, Jr. | ............... | 128/200.26 |
| 3,674,014 A | | 7/1972 | Tillander | | |
| 3,996,939 A | * | 12/1976 | Sheridan et al. | ........ | 128/207.14 |
| 4,170,232 A | * | 10/1979 | Khoury | ....................... | 600/581 |
| 4,244,362 A | * | 1/1981 | Anderson | .............. | 128/200.26 |
| 4,431,005 A | * | 2/1984 | McCormick | ................ | 600/433 |
| 4,444,185 A | * | 4/1984 | Shugar | .................. | 128/207.29 |
| 4,445,501 A | * | 5/1984 | Bresler | ........................ | 600/12 |
| 4,567,882 A | * | 2/1986 | Heller | ......................... | 600/249 |
| 4,593,687 A | * | 6/1986 | Gray | ..................... | 128/200.26 |
| 4,735,607 A | | 4/1988 | Keith, Jr. | | |
| 4,865,586 A | * | 9/1989 | Hedberg | .................. | 604/93.01 |
| 4,913,139 A | | 4/1990 | Ballew | | |
| 4,943,770 A | * | 7/1990 | Ashley-Rollman et al. | ...................... | 324/207.17 |
| 5,235,970 A | * | 8/1993 | Augustine | .............. | 128/200.26 |
| 5,257,636 A | * | 11/1993 | White | ......................... | 128/897 |
| 5,431,640 A | | 7/1995 | Gabriel | | |
| 5,560,351 A | * | 10/1996 | Gravenstein et al. | .. | 128/200.26 |
| 5,785,051 A | * | 7/1998 | Lipscher et al. | ........ | 128/207.15 |
| 5,996,582 A | * | 12/1999 | Turnbull | ................. | 128/207.29 |
| 6,161,537 A | * | 12/2000 | Gravenstein et al. | .. | 128/200.26 |
| 6,173,199 B1 | | 1/2001 | Gabriel | | |
| 6,349,720 B1 | * | 2/2002 | Clark | ..................... | 128/200.26 |
| 6,553,993 B2 | * | 4/2003 | Toti et al. | ............... | 128/207.14 |

* cited by examiner

Primary Examiner—Aaron J. Lewis
(74) Attorney, Agent, or Firm—Pitts & Brittian, PC

(57) ABSTRACT

A magnetically guided device for insertion through a patient's nasal passageway of a tube for feeding or lavage of a target organ. The device includes a flexible tube having an insertion end sized for insertion through the patient's nasal cavity, pharynx and esophagus. The tube insertion end includes a magnetic member rotatably coupled to the insertion end and a porous tube segment spaced-apart proximal of the magnetic member. The magnetic member is rotatable within the insertion end and is responsive to an externally positioned magnetic field that is moved relative to the patient for guiding the insertion end through internal passageways and into the target organ within the patient. A method for insertion and positioning of a magnetically guided tube for feeding or for lavage of a target organ within a patient is also disclosed.

21 Claims, 8 Drawing Sheets

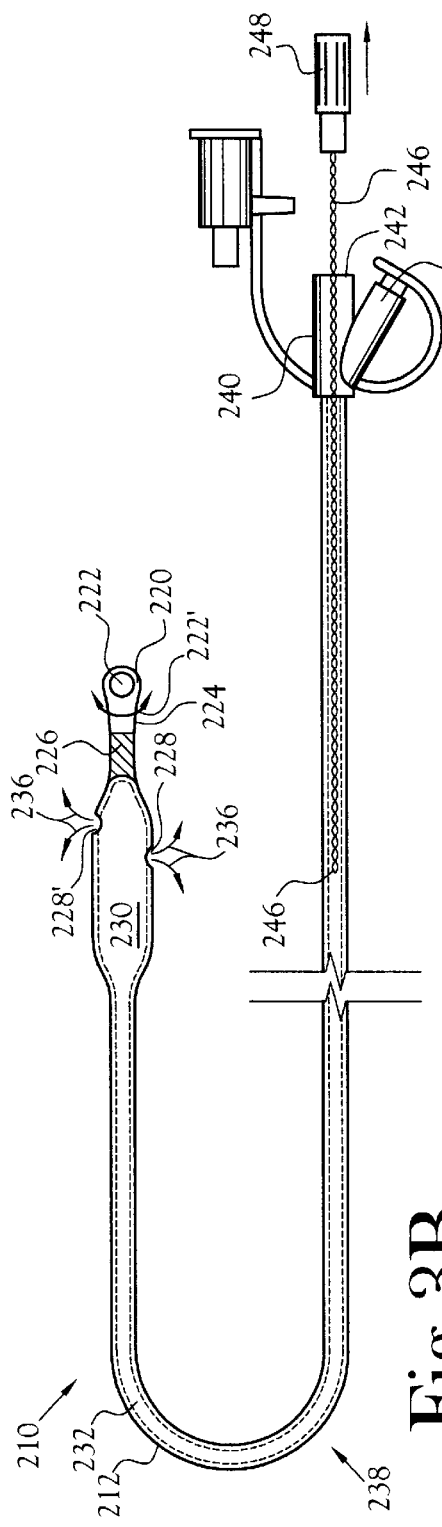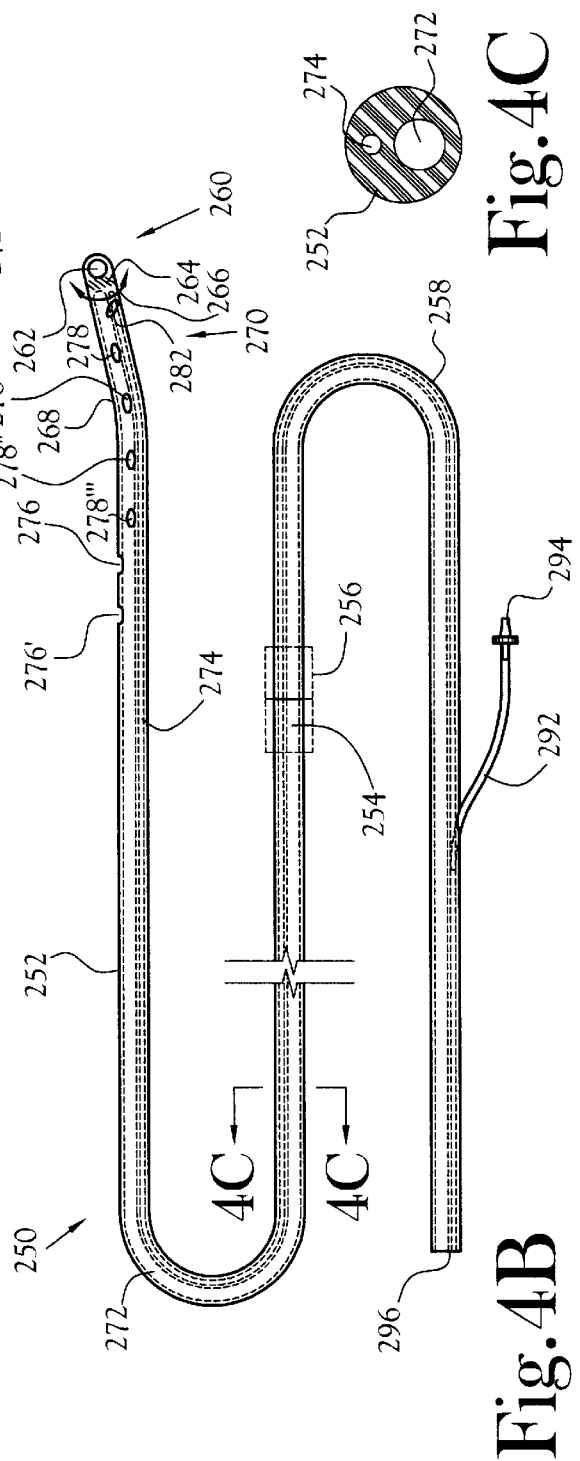

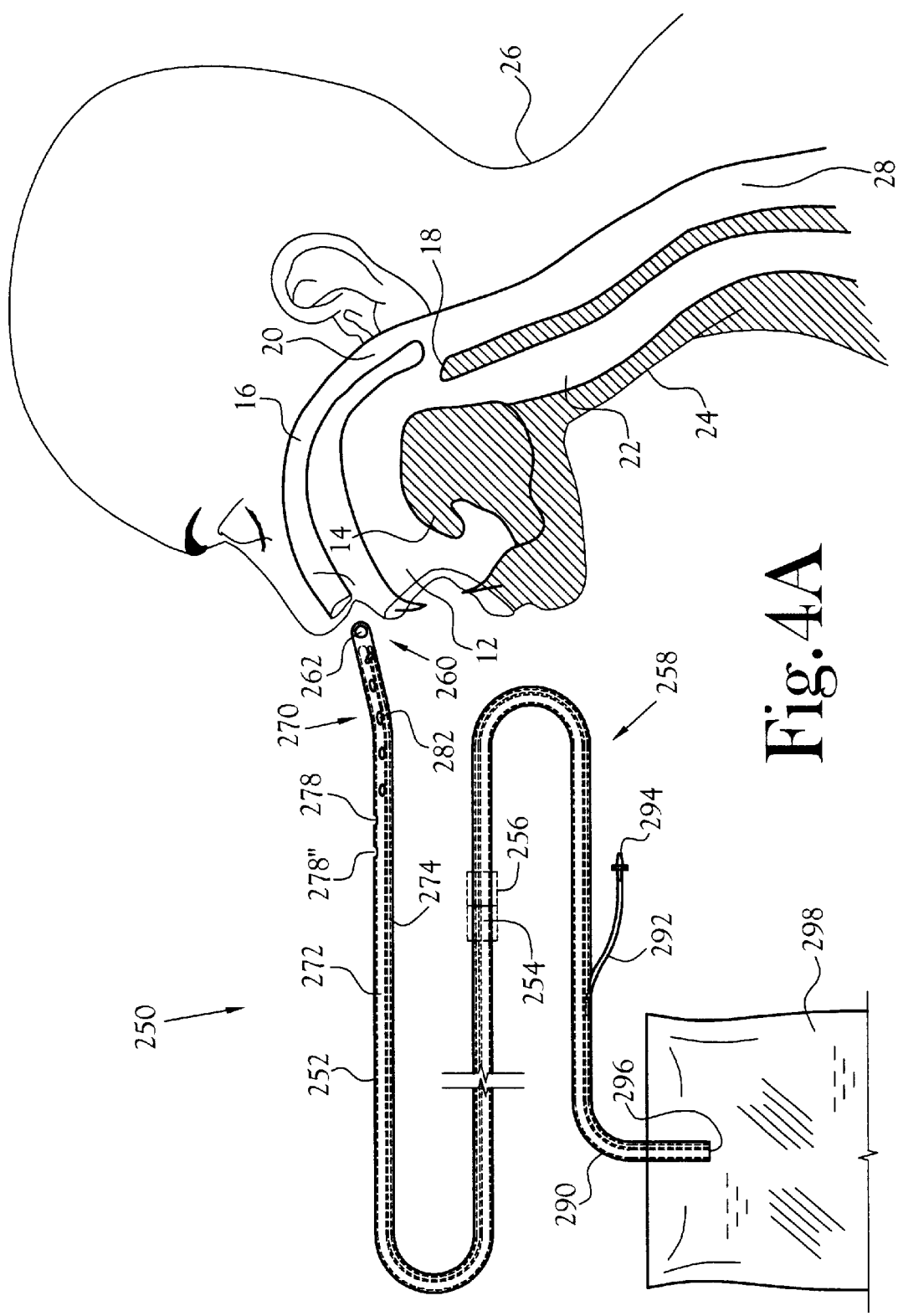

MAGNETICALLY GUIDED DEVICE FOR INSERTION THROUGH A NASAL PASSAGEWAY

CROSS REFERENCE TO RELATED APPLICATIONS

This is a continuation-in-part of application Ser. No. 10/207,602, filed Jul. 29, 2002, which is a continuation-in-part of application Ser. No. 10/078,133, filed Feb. 19, 2002.

STATEMENT REGARDING FEDERALLY SPONSORED RESEARCH OR DEVELOPMENT

Not Applicable.

BACKGROUND OF THE INVENTION

1. Field of Invention

This invention pertains to medical intubation devices for insertion of a tube into a patient. More particularly, this invention pertains to a nasal insertion device utilizing a magnetically guided tube for insertion into a patient's passageway and organ.

2. Description of the Related Art

Prior intubation devices have provided various guide mechanisms to direct a tube through appropriate passageways and into a target organ within a patient. Insertion of intubation devices is typically through the mouth and oral cavity for insertion into the esophagus, or through an incision in the abdominal wall for insertion into the stomach. Typical prior intubation device include insertion of a guide device such as a guide wire or stylet, an introducer sheath, and/or a guide cylinder, that is inserted into the mouth or nose for guiding of a feeding tube having an internal diameter sufficient for delivery of fluids into the patient's stomach or into the duodenum. A typical nasal feeding tube includes a guide wire that is inserted through the nasal cavity, or a feeding tube having a stylet inserted within the feeding tube which is inserted through the nasal cavity and pharynx. The stylet may include a braided length of metal wire that remains within the feeding tube during insertion to provide rigidity for the tube for inserting an insertion end of the feeding tube through the nasal cavity and pharynx, through the esophagus, and into the stomach. The metal wire or stylet is typically removed from the feeding tube after successful positioning of the tube insertion end through the preferred passageway and into the target organ. A typical method of insertion includes an operator's insertion of a feeding tube with stylet guide wire through the nasal cavity parallel to the nasal septum, advancing the feeding tube to the nasopharynx, allowing the insertion end to seek its own passage, and advancing the tube with a gentle motion through the esophagus and into the stomach. The gentle motion may include manipulation by twisting, rotating, and lateral turning of an external end held by a medical technician until the feeding tube insertion end is inserted into the esophagus and stomach. There are instances where a guide wire or a feeding tube having a stylet therein was improperly inserted into a sinus cavity or into the cranial cavity above the nasal cavity due to use of an improper procedure with excessive force.

Additional prior intubation devices include a nasogastric tube for removal of fluids and/or semi-solids from the stomach or duodenum. The nasogastric tube is inserted through the nasal cavity and pharynx for insertion through the esophagus and extension of an insertion end into the stomach. The nasogastric tube includes two conduits within the tubes that are aligned along the interior length of the tube, with one conduit intended for passage of air into the stomach to replace liquids removed from the stomach through a second conduit within the tube. The nasogastric tube insertion end includes a plurality of holes positioned laterally through the tubular wall for suction of fluids into the second conduit for transfer to an exterior collection container. The tubular walls of the nasogastric tube are generally more rigid than a typical feeding tube in order to minimize internal collapse of the walls when suction is applied. Due to the lesser flexibility in comparison with similar lengths of feeding tubes, the nasogastric tube is more difficult to position through the nasal cavity, pharynx and through the esophagus for insertion into the stomach. A tube having an insertion end with an internal guiding device that is influenced by an external guiding force would provide improved insertion of a feeding tube or a nasogastric tube while minimizing improper placement of the tube insertion end into a patient's sinus cavity, brain cavity, or trachea.

There is a need for a fluid transfer tube that is externally guided through internal passageways and into a target organ within a patient. A further need includes providing a magnetically guided tube insertion end for insertion through the nasal cavity and through internal passageways for placement into a patient's target organ.

BRIEF SUMMARY OF THE INVENTION

According to one embodiment of the present invention, a medical device is disclosed for insertion of a tube having a magnetically guided insertion end into a patient for transfer of fluids between the tube and a target organ. The tube includes a flexible length of tubing having an insertion end sized for insertion into the patient's nasal cavity. A magnetic member is rotatably coupled within the insertion end. The magnetic member is freely rotatable within the insertion end during insertion through internal passageways for insertion into the target organ within the patient. The insertion end includes a porous tube segment proximal to the rotatable magnetic member for transfer of fluids between tube and the target organ. An externally maintained end of the tube is attachable to a supply of fluids or is attachable to an external collection container. The magnet member is enclosed within an end enclosure distal of the porous tube segment thereby allowing transfer of fluid through the tube insertion end without affecting the rotation of the magnetic member. When inserted through the nasal cavity, the rotatable magnetic member and insertion end are remotely guided by manipulation of an external magnetic field positioned proximal to the patient. The external magnetic field is moved relative to the patient in order to guide the insertion end into the target organ. The magnetically guided tube insertion end provides rapid insertion through internal passageways and into the target organ without insertion of an optic viewing device or a channeling device in the patient. A method for insertion of a magnetically guided tube into a patient's target organ by manipulation of an external magnetic field is also disclosed herein.

BRIEF DESCRIPTION OF THE SEVERAL VIEWS OF THE DRAWINGS

The above-mentioned features of the invention will become more clearly understood from the following detailed description of the invention read together with the drawings in which:

FIG. 3B is an exploded side view of FIG. 3A, illustrating the rotatable magnetic member disposed in the feeding tube insertion end;

FIG. 4A is a side perspective view of a magnetically guided nasogastric tube of the present invention for insertion through a nasal passageway and into the stomach;

FIG. 4B is an exploded side view of FIG. 4A illustrating the rotatable magnetic member disposed in the nasogastric tube insertion end;

FIG. 4C is a section view along 4C—4C of FIG. 4B of a first and a second conduit within the nasogastric tube;

DETAILED DESCRIPTION OF THE INVENTION

Figure 1:
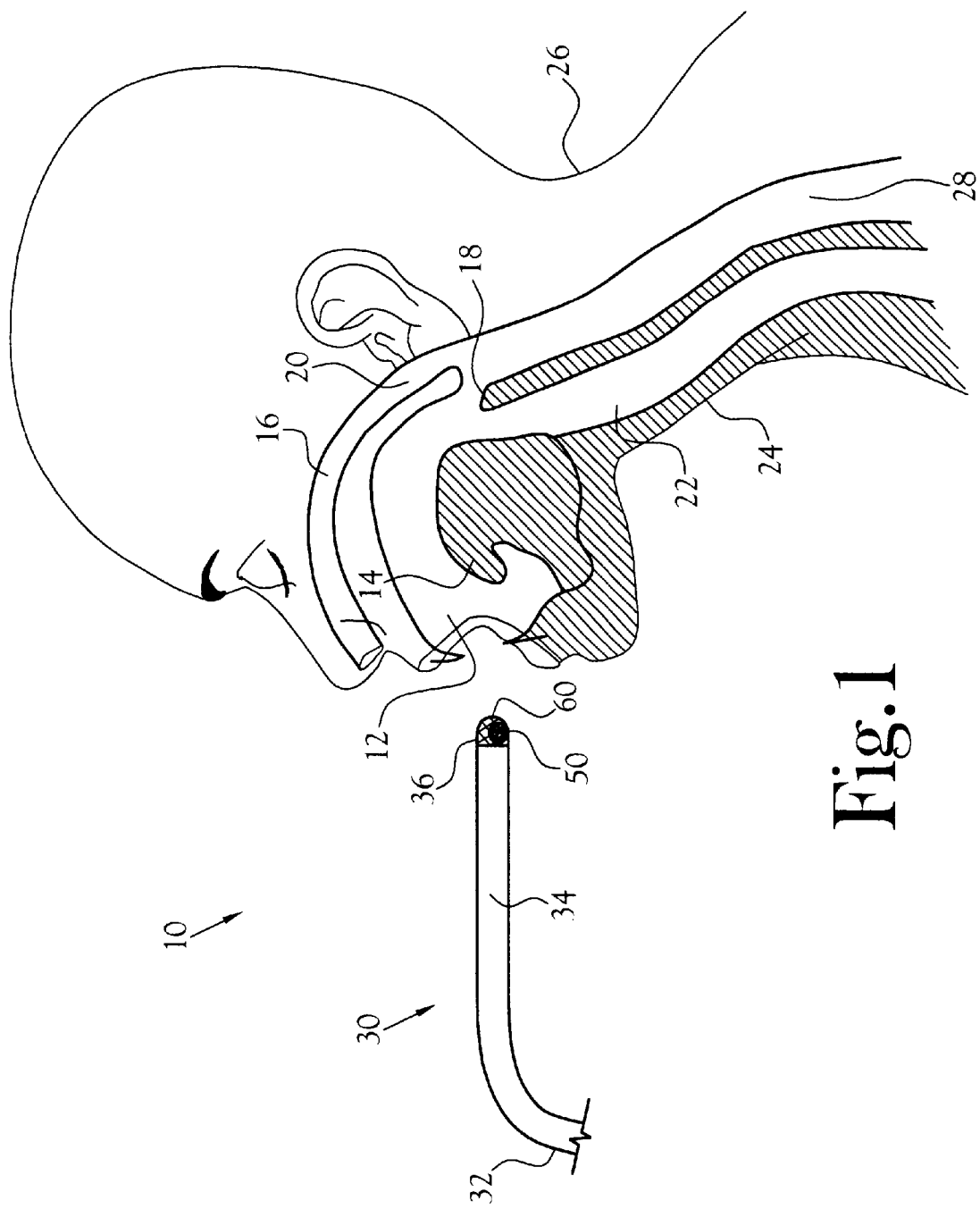
FIG. 1 is a side view of an intubation tube having a rotating magnetic guide disposed on an insertion end of the tube for insertion through a patient's oral cavity.

As illustrated in FIG. 1, a rotating magnetic intubation device 10 is disclosed for a rapid intubation procedure by a properly trained operator for insertion of a substantially hollow intubation tube 30 into a patient's oral cavity 12 (see FIG. 1), past the tongue 14, into the oral cavity 16, and past the glottic opening 18 and vocal cords for passage into a patient's trachea 22 or esophagus 28. The intubation tube 30 includes flexible side walls and an internal channel for transfer of air or fluids into the patient. The intubation tube 30 includes an external first end 32 held by the operator, a flexible mid-portion 34, and a distal insertion end 36 having a rotating magnet 50 positioned within a porous enclosure 60 attachable on the insertion end 36 of the intubation tube 30 (see FIG. 1). The rotating magnet 50 includes a generally spherical magnet that is freely rotatable within the porous enclosure 60 such as a containment shell having a plurality of holes through which fluids can flow without being occluded by the magnet 50. The magnet 50 is typical of magnets known to those skilled in the art, having north and south orienting portions, and is guided along with the insertion end 36 through the patient's internal passageways by a magnetic field moved external of the patient.

Figure 2:
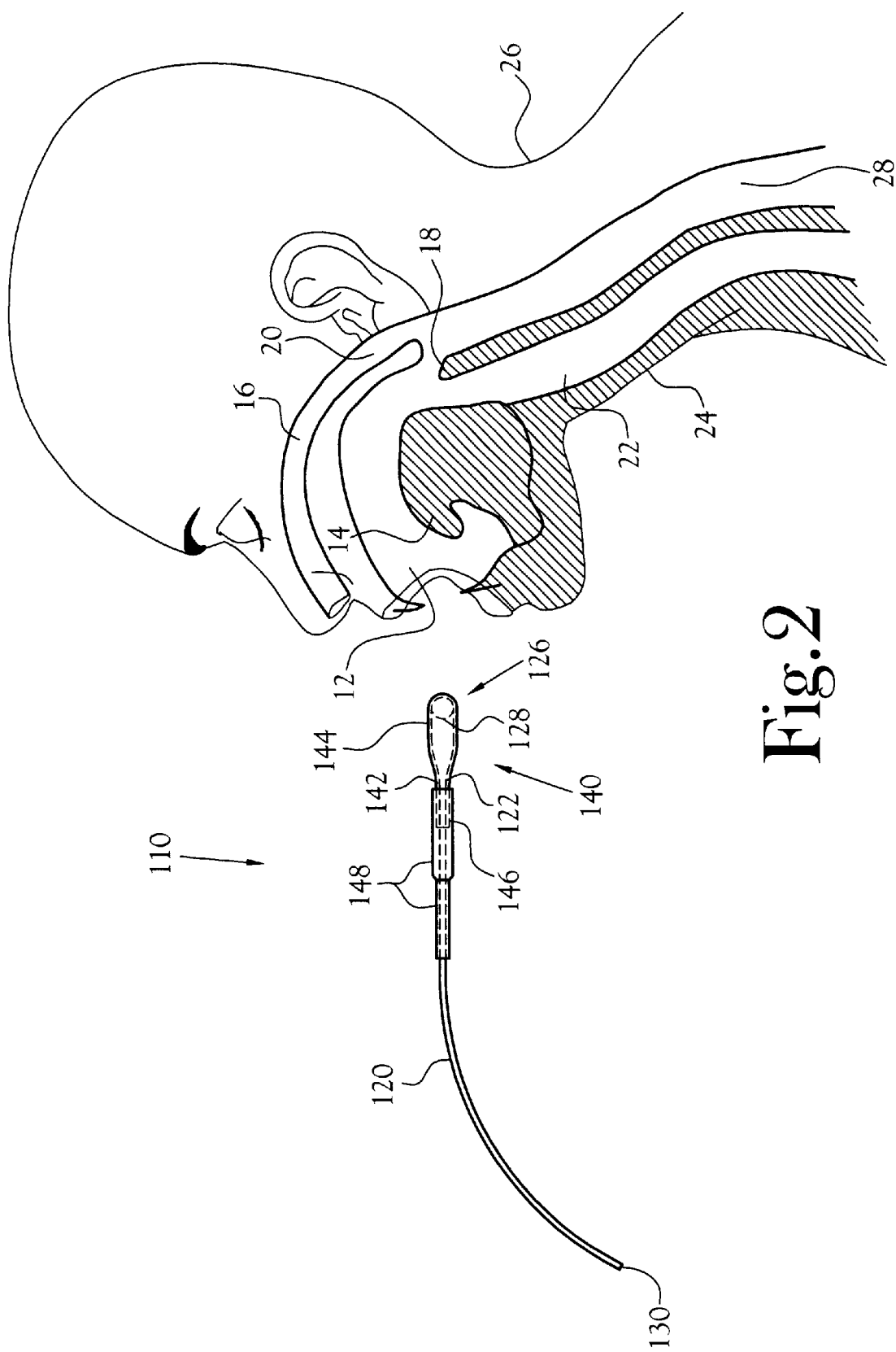
FIG. 2 is a side view of an insertion blade device having a rotating magnet member disposed on an insertion end for insertion through a patient's oral cavity.

As illustrated in FIG. 2, a magnetic oral laryngeal elevator (mole) intubation blade 110 is disclosed for insertion of the intubation blade 110 into a preferred pathway within a patient such as a trachea 22 or an esophagus 28. The intubation blade 110 includes an elongated body 120 having an insertion end 126 and a magnetic member 128 coupled thereon. The magnetic member 128 is flexibly coupled proximal to a distal end 122 of the elongated body 120 to allow pivoting of the magnetic member 128 in relation to the distal end 122. The magnetic member 128 is enclosed in a flexible tubular sleeve 140 composed of resilient material having a rounded, closed enclosure end 144, a flexible throat segment 142, and a tube connector end 146 that is joined to the distal end 122. The flexible member 140 is composed of material such as a medical grade silicone, latex rubber material, or a comparable surgical grade material that bendable both laterally and longitudinally. The tube connector end 146 is attached to the distal end 122 of the elongated body 120 by a sleeve 148 of connecting material that encloses both the tube connector end 146 and the distal end 122. The sleeve 148 is composed of a thermo-plastic material such as a polyolefin tubing having an adhesive lined interior, for firmly attaching the tube connector end 146 onto the distal end 122. During insertion of the insertion end 126 into the patient, the orientation of the magnetic member 128 is influenced by a magnetic field external of the patient. The magnetic member 128 and insertion end 126 are guided by the movement of the external magnetic field along the patient's dermal surface in order to guide the insertion end 126 into a preferred internal passageway. Upon positioning of the insertion end 126 into the preferred passageway, an intubation tube is inserted therein by guiding along the path of the elongated body 120.

Figure 3A:
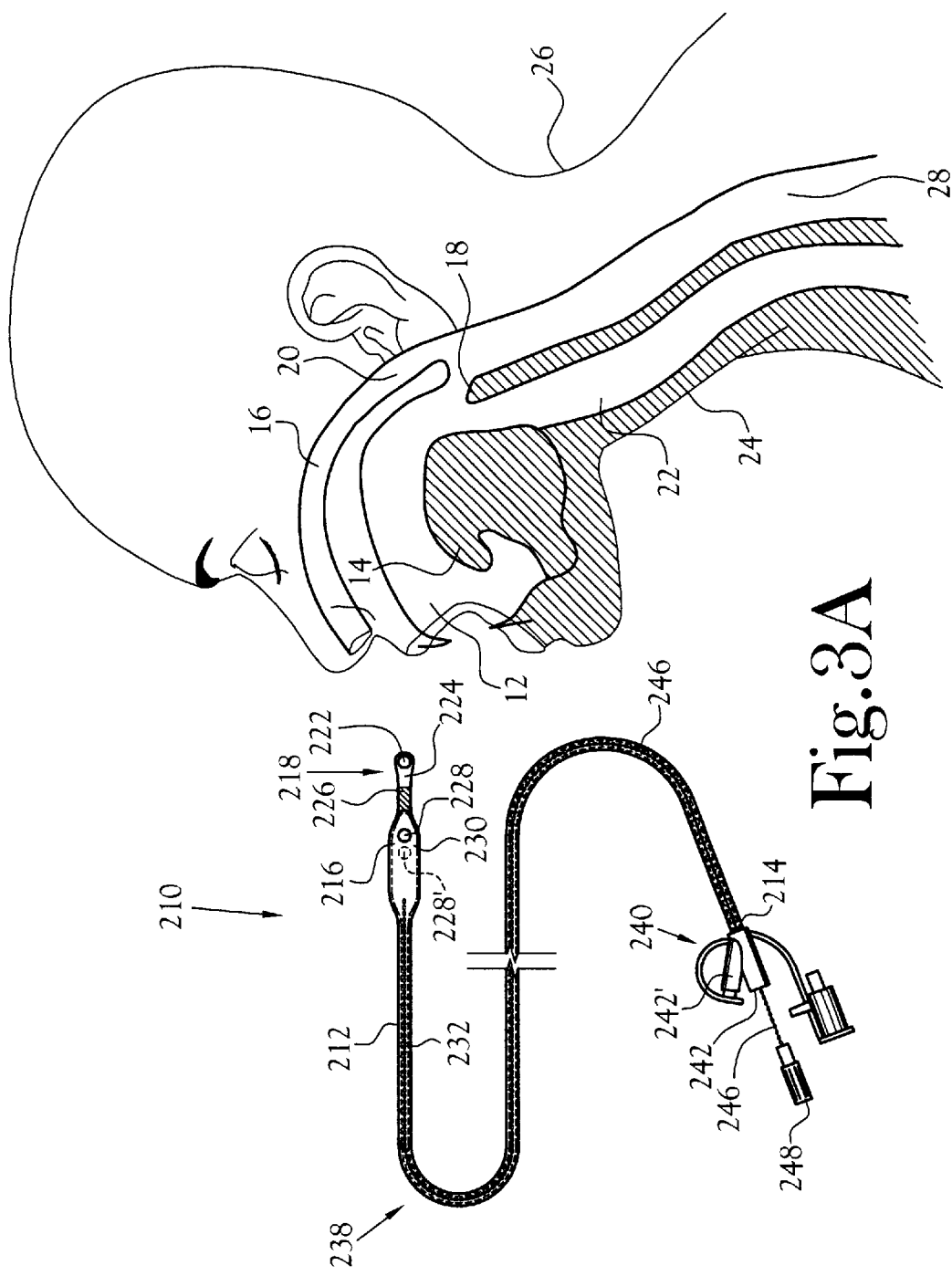
FIG. 3A is a side perspective view of a magnetically guided feeding tube of the present invention for insertion through a nasal passageway and into the stomach.

As illustrated in FIGS. 3A and 3B, a magnetically orienting medical device is disclosed for insertion through the patient's nose and nasal cavity 16 for use as a nasal feeding tube 210. The nasal feeding tube 210 includes an elongated flexible tube 212 that is easily bendable 238 laterally and longitudinally, and includes a sufficient length to allow an insertion end 218 of the tube 212 to be inserted through the nasal cavity, through the pharynx 20 and esophagus 28 and into the patient's stomach 40 for transfer of fluids into the stomach 40. The tube 212 includes a proximal end 214 that is maintained external of the patient, and includes valve connector 240 maintained external of the patient for connection to a plurality of access ports 242, 242' of a liquid flushing tube, irrigation syringe, and/or a container 244 of liquid supplement. The proximal end 214 is sized to allow a steel stylet 246 to be inserted through the tube 212 during insertion of the feeding tube 210 into the patient. The steel stylet 246, when inserted completely in the length of the feeding tube 210, provides stiffness along the longitudinal length of the tube 212 to facilitate positioning of the insertion end 218 through the nasal cavity 16 and through the pharynx 20. After the insertion end 218 is inserted through the preferred internal passageways and into the stomach 40 as guided by externally positioned magnets 80, 84, the steel stylet 246 and capped end 248 are removed to provide a more flexible length of tube 212 that is less irritating to the patient's internal passageways. A sufficient length of the steel stylet 246, and the tube 212 may range from about 12 inches to about 24 inches in length for insertion into children, or about 36 inches to about 48 inches for insertion into adults.

The insertion end 218 is generally cylindrical and sized to fit through either of the nostrils of the patient's nose and through the nasal cavity 16, the pharynx 20 and the esophagus 28. A fluid flow 234 within the tube interior 232 is maintained by a upstream pressure gradient or gravity flow between the external container 244 and the tube interior 232 for flow into an internal void space 230 proximal to the insertion end 218. The internal void space 230 is enclosed by a porous tube segment 216 including at least one exit port 228, and preferably a second exit port 228' for transfer 236 of liquids into the stomach 40. A rotatable magnet member 222 is disposed within the insertion end 218 in an end enclosure 220 that is segregated from the void space 230 by a partition 224 that allows the freely rotatable magnet 222 to remain apart from the void space 230 in order to not hinder the transfer of fluids through the respective exit ports 228, 228' of the porous tube segment 216. The insertion end 218 may include radiopaque material 226 for tracking of the progress of the insertion end in the patient by appropriate external equipment.

Figure 5:
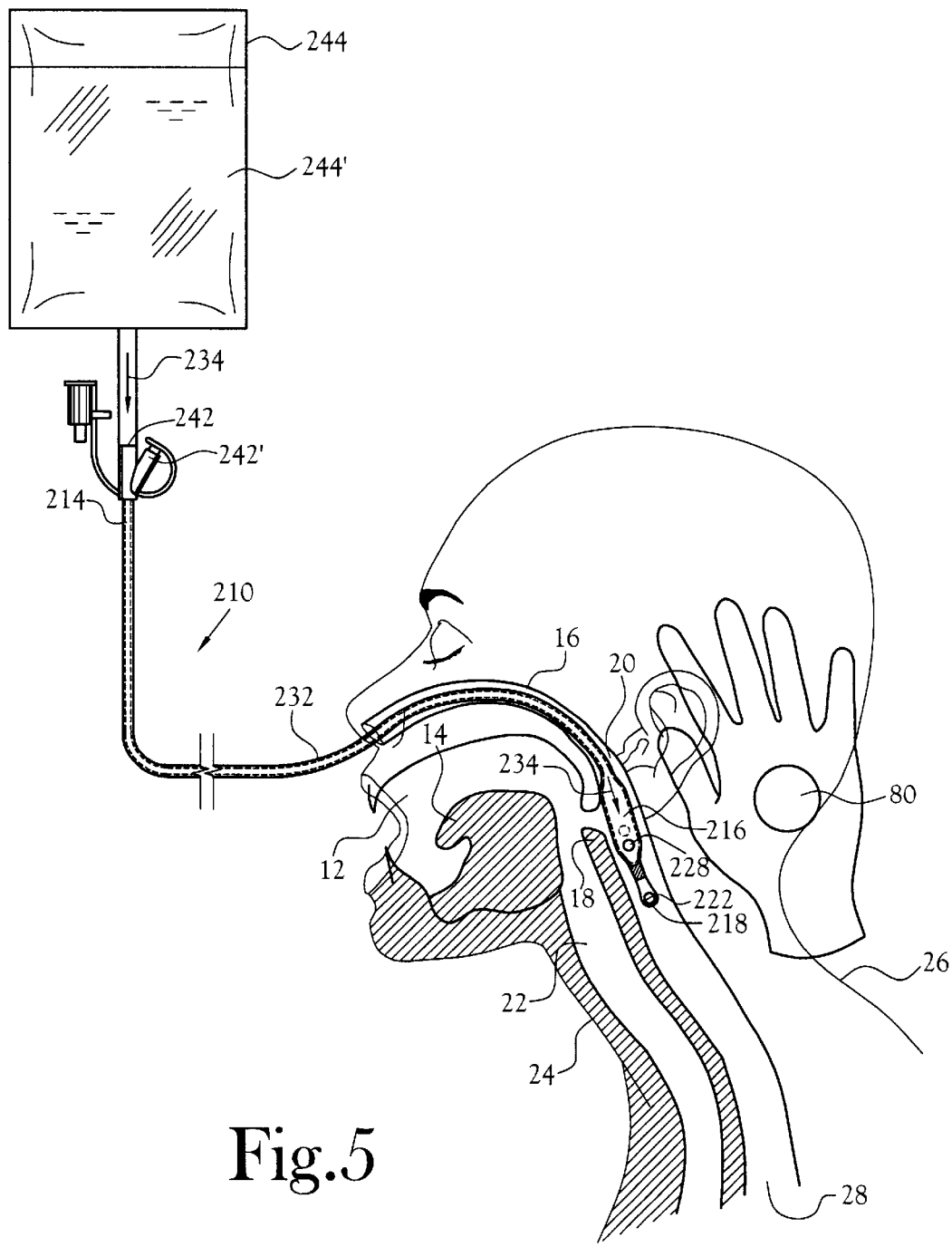
FIG. 5 is a perspective side view of the magnetically guided feeding tube of FIG. 3A inserted into the esophagus upon guidance by an external magnetic field.
Figure 7:
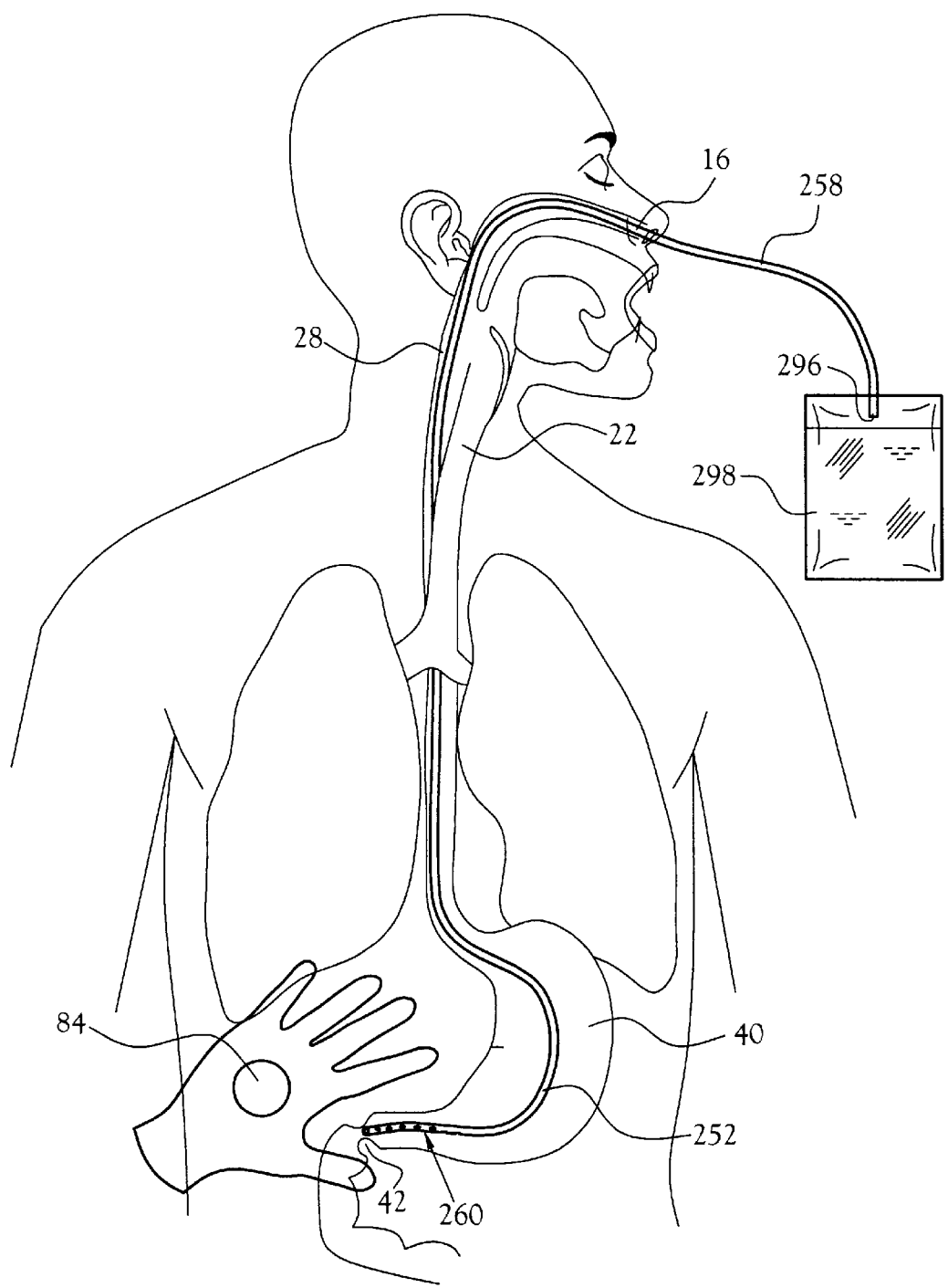
FIG. 7 is a perspective side view of the magnetically guided nasogastric tube of FIG. 6 extended into the stomach and the duodenum of the patient upon guidance by an external magnetic field manipulated by an operator.

The rotatable magnet member 222 is preferably a spherical shape for rotation 222' (see FIG. 3B) and re-orientation of the magnet's north and south poles in response to an external magnetic field provided by one or more external magnets 80, 84 held by an operator proximal to the patient. The rotatable magnet member 222 may alternately be composed of ferro-magnetic material responsive to movement of an external magnetic field. The response of the rotatable magnet member 222 upon being attracted or repelled from the external magnets 80, 84 provides a responsive insertion end 218 that is remotely guided past branching passageways such as the glottic opening 18. Upon movement of the external magnets 80, 84 along the patient's dermal surfaces, the rotatable magnet member 222 and insertion end 218 are guided through respective internal passageways and into the stomach 40. After guiding the insertion end 218 into the stomach (see FIG. 5), feeding fluids and/or liquids containing medication are transferred 236 into the stomach 40. Alternately, the insertion end 218 having the magnet member 222 therein can be further inserted through the stomach 40 and guided by one or more external magnets 80, 84 held by an operator proximal to the patient (see FIG. 7). When the insertion end 218 is positioned past the pyloric canal 42 leading to the duodenum 44, the feeding fluids and/or medication are transferred 236 into the duodenum 44.

Figure 6:
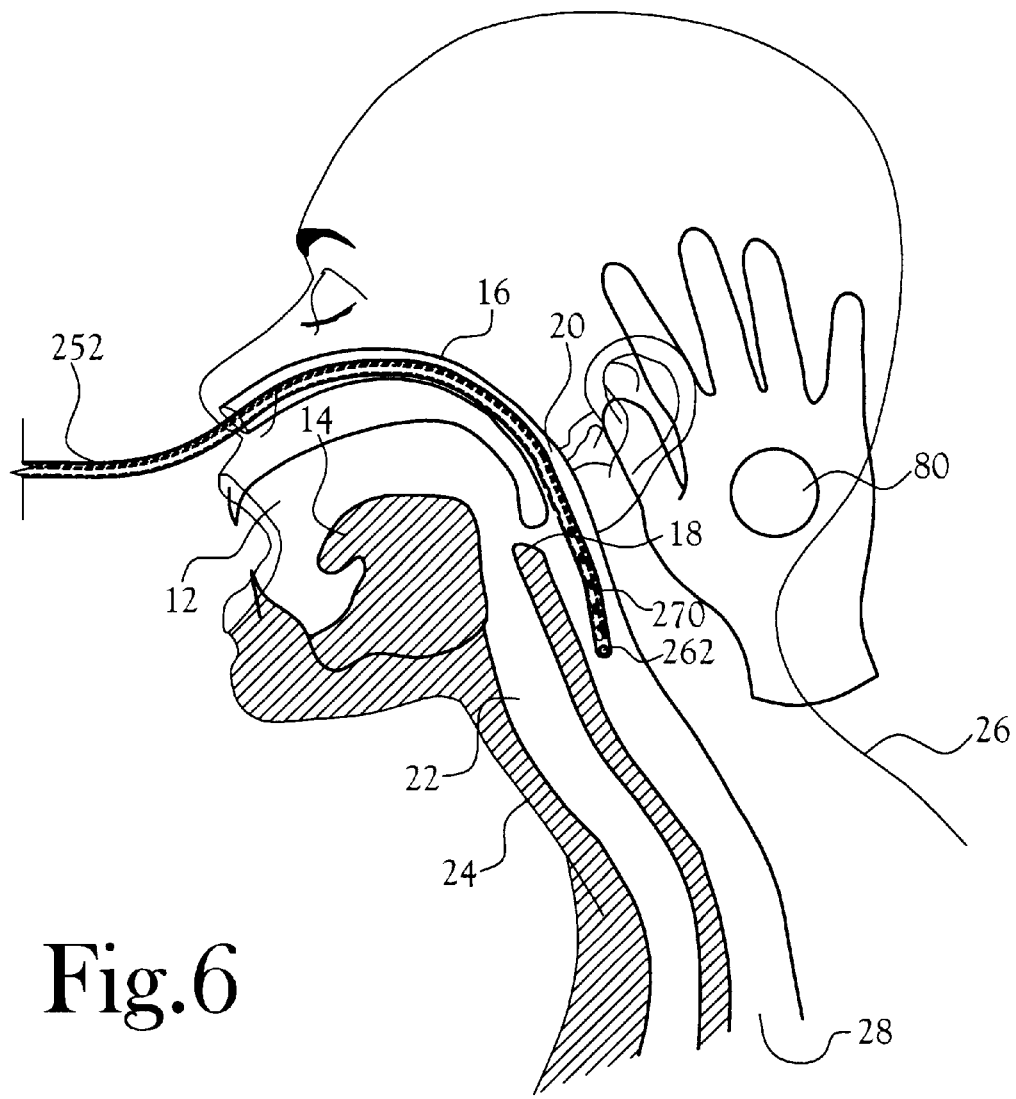
FIG. 6 is a perspective side view of the magnetically guided nasogastric tube of FIG. 4A inserted into the esophagus upon guidance by an external magnetic field.

An alternative embodiment of the present invention is illustrated in FIGS. 4A and 4B as a nasogastric tube 250 that includes an elongated tube member 252 having an insertion end 260 guided by a magnetic member 262 disposed therein, for insertion of the insertion end 260 into the stomach 40 or duodenum 44 to facilitate removal of liquids and semi-solids from within the patient. The elongated tube member 252 includes a connector end 254 that is attachable to an extension tubing 258 that is of a sufficient length to extend out of the patient to an exit port 296 for transfer to a receptor bag or container 298 of liquids removed from the patient's target organ such as the stomach 40. The elongated tube member 252 and the extension tubing 258 have similar internal construction including two internal conduits that provide for transfer of liquids through a first, major conduit 272 and provide for transfer of air through a second conduit 274. An internal void space 280 is enclosed by a porous tube segment 270 that is disposed within the insertion end 260 and proximal to the rotatable magnet 262. The void space 280 is separated from the magnetic member 262 by a partition 264 within the insertion end 260. Liquids and semi-solids are transferred from the target organ and through the porous tube segment 270 of the insertion end, with the porous tube segment 270 having a plurality of holes 276, 276', 278, 278', 278", 278'" for transfer by suction of fluids into the internal void space 280 for transfer through the major conduit 272 and transfer from exit port 296 and into the receptor bag or container 298 (see FIGS. 6 and 7).

The insertion end 260 of the nasogastric tube 250 is further illustrated in FIG. 4B and includes a generally elongated shape having a cylindrical cross-section. The insertion end 260 is sized to fit through either one of the nostrils of the patient's nose and through the nasal cavity 16, the pharynx 20 and the esophagus 28. Within a distal portion of the insertion end 260, a spherical magnetic member 262 is enclosed by a non-porous partition 264 that separates and allows the magnetic member 262 to freely rotate 266 (see FIG. 4B) in the distal portion of the insertion end 260 when a magnetic field is positioned external of the patient (see FIG. 6). The magnetic member 262 may include a spherical magnet having north and south magnetic fields, or a ferromagnetic member that is attracted to one or more external magnets 80, 84 positioned on one or more dermal surfaces of the patient. The rotatable magnet 262 serves as a radiopaque marker for remote projection of the progress of the insertion end 260 toward and into the target organ. Alternatively, a segment of the distal portion of the insertion end 260 may include a radiopaque marker 268. The rotatable magnet 262 and insertion end 260 are responsive to reorientation when influenced by external magnetic fields provided by external magnets 80, 84 positioned on one or more dermal surfaces of the patient (see FIG. 6). The external magnets 80, 84 may be positioned on the dermal surfaces proximal to the stomach 40 for repositioning and guidance of the rotatable magnet 262 and the insertion end 260 through the stomach 40 and into the duodenum 44 (see FIG. 7). The external magnets 80, 84, either individually or collectively, provide an external magnetic field of sufficient strength to guide the rotatable magnet 262 and insertion end 260 into the target organ in the patient.

Additional features of the elongated tube member 252 include flexible tube walls that bend laterally and longitudinally when inserted into the patient. The walls of the nasogastric tube 250 are generally more rigid than a similar length of the feeding tube 210 in order to prevent internal collapse of the walls of the tube member 252 when suction is applied for removal of liquids from the target organ. The tube walls are constructed of a medical grade plastic polymer that is of adequate flexibility to allow the nasogastric tube 250 to be positioned through the nasal cavity 16, pharynx 20, and esophagus 28 for insertion into the stomach 40 or duodenum 44. The interior of the extension tubing 258 is configured with a major conduit and a minor conduit with attachment of the connector end 254 of the elongated tube member 252 by a connector segment 256 to an adequate length of extension tubing 258 to provide for insertion of the insertion end 260 into an adult's or a child's stomach 40 or duodenum 44. At an exit end 290 of the extension tube 258 is an exit port 296 for discharge of fluids. Further, an air lumen vent tube 292 and an anti-reflux valve 294 are connected to the exit end 290 for transfer of gas or liquids between an insertion end vent opening 282 that is in communication with the second, minor conduit 274 at the insertion end 260. The second conduit 274 and end vent opening 282 allows for transfer of air, gas, and medicinal liquids into and out of the patient's target organ to provide protection of the patient's target organ from collapse from the suction pressure applied through the major conduit 272 during removal of liquids through first conduit 272 from the target organ. An aspirator device (not shown) such as a vacuum system known to those skilled in the art is connectable to the exit end 290 of the nasogastric tube 250 for maintenance of a suction pressure along the major conduit 272.

A method of insertion of a magnetically guided nasal tube is also disclosed for rapid insertion through the nasal cavity 16, pharynx 20 and esophagus 28 for insertion of the tube into a target organ such as the stomach 40 or the duodenum 44. The magnetically guided nasal tube may be inserted into other target organs depending on the internal passageways and internal valves and constriction barriers that disposed between an opening in the patient, either a natural orifice or a surgical incision, and the target organ. A step of using includes providing a flexible elongated tube such as a feeding tube 210 or a nasogastric tube 250 having an insertion end in which a rotatable magnetic member is enclosed. A step of inserting includes positioning the insertion end having the rotatable magnetic member therein, through the nasal cavity 16 and the pharynx 20. A step of guiding proceeds simultaneously with the step of inserting, with the step of guiding includes positioning one or more external magnets 80, 84 on the patient's dermal surfaces near the pharynx 20 and the esophagus 28, with the external magnets having a magnetic field of sufficient strength for attracting or repelling the rotatable magnet along the preferred passageway within the patient (see FIGS. 5 and 6). A step of positioning includes remotely adjusting the path of the insertion end into the target organ, such as the stomach 40 or duodenum 44, by guiding the one or more external magnet 80, 84 along the dermal surface of the patient's throat, neck and abdomen areas (see FIG. 7). The step of positioning remotely adjusts the position of the insertion end into the appropriate target organ 40. An additional step of repositioning may be included to provide for repositioning the one or more external magnets 80, 84 along the dermal surface of the patient's lower abdomen area in order to remotely adjust the path of the insertion end and magnetic member past the pyloric canal 42 and into the duodenum 44. An additional step of transferring fluids may follow the step of positioning, and the step of repositioning, in order to transfer feeding fluids through the elongated feeding tube 210 and into the stomach 40, or to remove fluids through the elongated nasogastric tube 250 from the stomach 40 or duodenum 44. When the transfer of fluids is complete, the elongated feeding tube 210 or nasogastric tube 250 may be removed from the respective internal passageways and from the nasal cavity 16.

From the foregoing description, it will be recognized by those skilled in the art that the elongated feeding tube 210 and the elongated nasogastric tube 250 provide an insertion device that is guided by an externally positioned magnetic field for insertion through a nasal passageway, through preferred passageways and into a target organ without requiring direct visual observations of the respective passageways within the patient. An additional benefit includes a rotatable magnetic member guiding tubular member that is removably insertable through a patient's internal passageways and into a target organ without insertion of additional internal guide channels or guide wires during positioning and repositioning of the tubular member within the patient.

While the present invention has been illustrated by description of several embodiments and while the illustrative embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicants' general inventive concept.

Having thus described the aforementioned invention, we claim:

1. A medical device for insertion through a patient's internal passageways and into a target organ, comprising:
   a flexible tube for transfer of fluids between a patient's target organ and the exterior of the patient; said tube having an insertion end sized for insertion into an opening in the patient, said insertion end including a non-porous end segment extended distal of a porous tube segment disposed along said tube insertion end;
   a magnetic member rotatably disposed within said non-porous end segment of said tube insertion end, said magnetic member rotates within said non-porous end segment without occluding the flow of fluids through said porous tube segment of said tube insertion end; and
   a magnetic field positioned external of the patient, said external magnetic field is manipulated to affect the orientation of said magnetic member within the patient;
   whereby said external magnetic field is moved relative to the patient for guiding said magnetic member and said insertion end through a preferred passageway and into the target organ within the patient.

2. The medical device of claim 1 wherein said insertion end including said porous tube segment extended along said tube a spaced apart distance medial from said non-porous end segment, said rotatable magnetic member rotatably disposed within said non-porous end segment of said insertion end, said porous tube segment allows transfer of fluids from said flexible tube and into the target organ upon passage of said insertion end into the target organ of the patient.

3. The medical device of claim 2 wherein the opening of the patient is the patient's nasal cavity and the preferred passageway is the esophagus of the patient.

4. The medical device of claim 3 wherein said porous tube segment includes at least two holes disposed on opposed sides of said porous tube segment, said holes provide for transfer of fluids from said flexible tube and into the target organ.

5. The medical device of claim 3 wherein said porous tube segment includes a plurality of holes disposed on opposed sides of said porous tube segment, said holes provide for transfer of fluids from said target organ and into said flexible tube for removal to a collection container releasably connected to a proximal tube end maintained external of the patient.

6. The medical device of claim 3 wherein said rotatable magnetic member includes a spherical magnet enclosed by said non-porous end segment distal of said porous tube segment, said spherical magnet is disposed said spaced apart distance distally apart from said porous tube segment, said spherical magnet rotates when in the presence of said external magnetic field moved along a dermal surface of the patient.

7. The medical device of claim 3 wherein said rotatable magnetic member is composed of ferro-magnetic material responsive to movement of said external magnetic field moved along a dermal surface of the patient.

8. The medical device of claim 5 wherein said flexible tube includes a first and a second conduit within said tube for transfer of air through the first conduit and transfer of liquids through the second conduit, said second conduit provides removal of liquids from the stomach, said second conduit is connected to said plurality of holes of said porous tube segment proximal of said insertion end, said first conduit is connected to at least one hole of said plurality of holes of said porous tube segment.

9. The medical device of claim 8 wherein said external magnetic field includes at least one external magnet positioned against a dermal surface of the patient proximal to the passageway inside the patient, said at least one external magnet is manipulated along the dermal surface proximal to the internal passageway of the patient into which said insertion end is to be inserted.

10. The medical device claim 9 wherein said external magnetic field positioned external of the patient further includes at least one second external magnet positioned against a second location on the dermal surface of the patient proximal to the preferred passageway inside the patient, said at least one second external magnet is manipulated along the second location on the dermal surface proximal to the preferred passageway of the patient into which said insertion end is to be inserted.

11. A medical device for insertion of a tube through a nasal passageway and into a target organ within a patient, comprising:

a flexible tube having an insertion end sized for insertion through the patient's nasal cavity and through an internal passageway for extension into a target organ within the patient, said insertion end including a non-porous end segment;

a magnetic member rotatably disposed within said non-porous end segment of said insertion end;

a porous segment extended longitudinally along said tube proximal to said insertion end, said porous segment is disposed in spaced-apart relationship from said non-porous end segment having said magnetic member therein, said porous segment allows passage of gas and liquid between an interior of said flexible tube and the target organ; and a magnetic field positioned external of the patient, said external magnetic field is manipulated to affect the orientation of said magnetic member within the patient;

whereby upon insertion of said insertion end through the patient's nasal cavity and through the internal passageway of the patient, said rotatable magnetic member and insertion end are guided into the target organ when in the presence of said external magnetic field moved relative to the patient.

12. The medical device of claim 11 wherein said rotatable magnetic member is disposed within an end enclosure of said non-porous end segment for unhindered rotation of said magnetic member during transfer of air or liquids through said porous segment of said insertion end.

13. The medical device of claim 12 wherein said flexible tube includes at least two internal conduits extended through an interior of the axial length of said flexible tube, said at least two conduits are separately connected in fluid communication with said porous segment of said insertion end.

14. The medical device of claim 13 wherein said external magnetic field includes an external magnet positioned against a dermal surface of the patient proximal to the passageway inside the patient, said external magnet is manipulated along the dermal surface proximal to the internal passageway leading to the target organ within the patient, said external magnet having a magnetic field of sufficient strength to guide said rotatable magnetic member and insertion end into the target organ in the patient.

15. The medical device of claim 14 wherein said external magnetic field further includes a second external magnet positioned against a second location on the dermal surface of the patient proximal to the passageway inside the patient, said second external magnet is manipulated along the second location on the dermal surface proximal to the target organ in the patient into which said insertion end is inserted.

16. A medical device for insertion of a tube through a patient's nasal cavity and into a target organ, comprising:

a tube for transfer therethrough of fluids between a patient's target organ and the exterior of the patient, said tube having an insertion end sized for insertion into a nasal opening and through internal passageways leading to a target organ within the patient, a porous tube segment in spaced apart relationship from a distal end of said insertion end, said porous tube segment provides for transfer of fluids between said tube and the target organ within the patient;

a magnetic member rotatably disposed within a non-porous end segment in said distal end of said insertion end, said magnetic member is retained in said non-porous end segment extended distal of said porous tube segment whereby said magnetic member rotates without occluding the transfer of fluids through said porous tube segment; and a magnetic field positioned external of the patient, said external magnetic field is moved proximal to the patient for guidance of said magnetic member and said insertion end through the internal passageway and into the target organ within the patient.

17. The medical device of claim 16 wherein said rotatable magnetic member is composed of ferro-magnetic material responsive to movement of said external magnetic field moved proximal to and along a dermal surface of the patient.

18. The medical device of claim 17 wherein said external magnetic field includes an external magnet positioned against the dermal surface of the patient for guidance of said magnetic member and said insertion end through the target organ and into a second target organ within the patient.

19. The medical device of claim 18 wherein said tube includes a first and a second conduit extended lengthwise within said tube, said first conduit provides for transfer of fluids between said porous tube segment and the target organ, said second conduit provides for transfer of fluids from said second conduit separate of the fluids transferred through said first conduit, said second conduit is connected to at least one hole in said porous tube segment in spaced-apart relationship with said non-porous end segment of said insertion end, said first conduit is connected to at least one additional hole in said porous tube segment in spaced-apart relationship with said non-porous end segment, whereby fluids are transferred between either one of said first conduit and said second conduit in said tube and the target organ without fluid contact with said magnetic member rotatably disposed in said non-porous end segment of said insertion end.

20. A method for insertion of a magnetically guided tube through a patient's internal passageways and into a target organ of a patient, comprising the steps of:

using a fluids transfer tube including an insertion end having a non-porous distal end segment containing a magnetic member disposed in a rotating configuration therein;

inserting said fluids transfer tube through a nasal cavity of the patient;

guiding said fluids transfer tube through the patient's nasal cavity and through internal passageways leading to a target organ by guiding the path of said magnetic member and said insertion end into the respective internal passageways by positioning an external magnetic field proximal to a dermal surface of the patient;

positioning said external magnetic field along the dermal surface of the patient for remotely adjusting the position of said magnetic member and said insertion end within the respective internal passageways for insertion into the target organ; and transferring fluids between a porous tube segment of said fluids transfer tube and the target organ, said step of transferring fluids from said porous tube segment does not interfere with the rotation of said magnetic member within said non-porous end segment spaced apart from said porous tube segment proximal of said insertion end positioned within the target organ in the patient, whereby fluids are transferred during said step of transferring without contacting said magnetic member.

21. The method for insertion of claim 19 wherein said step of positioning further includes a step of repositioning said external magnetic member along the dermal surface of the patient for guiding said magnetic member and said insertion end into a second target organ within the patient.

* * * * *